United States Patent [19]

Heckel et al.

[11] Patent Number: 5,008,290
[45] Date of Patent: Apr. 16, 1991

[54] SULPHONAMIDOETHYL COMPOUNDS AND PHARMACEUTICAL COMPOSITIONS COMPRISING THESE COMPOUNDS

[75] Inventors: Armin Heckel; Josef Nickl; Erich Muller; Berthold Narr; Johannes Weisenberger; Wolfgang Eisert; Thomas Muller, all of Biberach, Fed. Rep. of Germany

[73] Assignee: Dr. Karl Thomae GmbH, Biberach an der Riss, Fed. Rep. of Germany

[21] Appl. No.: 319,397

[22] Filed: Mar. 3, 1989

Related U.S. Application Data

[62] Division of Ser. No. 92,742, Sep. 3, 1987, Pat. No. 4,870,076.

[30] Foreign Application Priority Data

Sep. 3, 1986 [DE] Fed. Rep. of Germany ....... 3629929

[51] Int. Cl.[5] ..................... A61K 31/34; C07D 307/54
[52] U.S. Cl. ................................... 514/544; 514/471; 549/60; 549/488; 549/494
[58] Field of Search .......................... 549/60, 488, 494; 514/444, 471

[56] References Cited

U.S. PATENT DOCUMENTS 4,752,613 6/1988 Floyd et al. ..................... 514/438

FOREIGN PATENT DOCUMENTS 031954 7/1981 European Pat. Off. .

OTHER PUBLICATIONS

Fréhel et al., J. Het. Chem, vol. 22, No. 4 (1985) pp. 1011–1016.

Primary Examiner—Richard L. Raymond
Attorney, Agent, or Firm—David E. Frankhouser; Mary-Ellen M. Timbers; Alan R. Stempel

[57] ABSTRACT

The invention relates to new sulphonamidoethyl compounds having valuable pharmacological properties, particularly anti-thrombotic properties, and which are also thromboxane antagonists.

6 Claims, No Drawings

SULPHONAMIDOETHYL COMPOUNDS AND PHARMACEUTICAL COMPOSITIONS COMPRISING THESE COMPOUNDS

This is a division of U.S. application Ser. No. 092,742, filed Sept. 3, 1987, now U.S. Pat. No. 4,870,076.

The present invention relates to new sulphonamidoethyl compounds of general formula

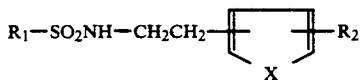

(I)

the enantiomers and the addition salts thereof, and, particularly, for pharmaceutical use, the physiologically acceptable addition salts thereof with inorganic or organic bases if $R_2$ contains a hydroxycarbonyl group, which have valuable pharmacological properties, particularly antithrombotic activity, whilst the new compounds are also thromboxane antagonists.

The present invention therefore relates to the new compounds of general formula I above, the enantiomers thereof if the group $R_2$ contains an optically active carbon atom, the addition salts thereof with inorganic or organic bases and, particularly for pharmaceutical use, the physiologically acceptable addition salts thereof, pharmaceutical compositions containing these compounds and processes for preparing them.

In the general formula given above $R_1$ represents a phenyl group optionally mono-, di- or trisubstituted by a halogen atom or by a methyl or methoxy group, the substituents being identical or different, or a benzyl, nitrophenyl, acetamidophenyl or thienyl group, $R_2$ represents a hydroxycarbonyl or alkoxycarbonyl group with a total of 2 to 4 carbon atoms bonded via a straight-chained or branched alkylene group with 1 to 5 carbon atoms or via an alkenylene group with 2 to 5 carbon atoms, whilst a methylene group in the above-mentioned alkylene or alkenylene groups, which must be linked to the heterocyclic group, may be replaced by a hydroxymethylene or carbonyl group, or a 4,5-dihydro-pyridazin-3-on-6-yl or pyridazin-3-on-6-yl group optionally substituted in the carbon structure by an alkyl group with 1 to 3 carbon atoms, and X represents an imino group optionally substituted by an alkyl group with 1 to 3 carbon atoms, or an oxygen or sulphur atom.

As examples of the definitions given for the groups X, $R_1$ and $R_2$ above:

$R_1$ may represent a benzyl, phenyl, 2-methylphenyl, 3-methylphenyl, 4-methylphenyl, 2-methoxyphenyl, 3-methoxyphenyl, 4-methoxyphenyl, 2-fluorophenyl, 3-fluorophenyl, 4-fluorophenyl, 2-chlorophenyl, 3-chlorophenyl, 4-chlorophenyl, 2-bromophenyl, 4-bromophenyl, 3,4-dimethylphenyl, 3,4-dimethoxyphenyl, 2,4-difluorophenyl, 2,4-dichlorophenyl, 2,5-dichlorophenyl, 2,4-dibromophenyl, 4-methyl-2-chlorophenyl, 2,4,5-trichlorophenyl, 4-nitrophenyl, 4-acetamidophenyl or thien-2-yl group, $R_2$ may represent a hydroxycarbonylmethyl, 1-hydroxycarbonylethyl, 2-hydroxycarbonyl-ethyl, 1-hydroxycarbonyl-propyl, 3-hydroxycarbonyl-propyl, 1-hydroxycarbonyl-butyl, 4-hydroxycarbonyl-butyl, 1-hydroxycarbonyl-1-methyl-ethyl, 2-hydroxycarbonyl-1-methyl-ethyl, 2-hydroxycarbonyl-ethenyl, 2-hydroxycarbonyl-1-methyl-ethenyl, 3-hydroxycarbonyl- propenyl, 2-hydroxycarbonyl-ethanon-(1)-yl, 3-hydroxycarbonyl-n-propanon-(1)-yl, 4-hydroxycarbonyl- n-butanon-(1)-yl, 5-hydroxycarbonyl-n-pentanon-(1)-yl, 2-hydroxycarbonyl-2-methyl-ethanon-(1)-yl, 3-hydroxycarbonyl-2-methyl-n-propanon-(1)-yl, 3-hydroxycarbonyl-3-methyl-n-propanon(1)-yl, 4-hydroxycarbonyl-2-methyl-n-butanon-(1)-yl, 4-hydroxycarbonyl-3-methyl-n-butanon-(1)-yl, 4-hydroxycarbonyl-4-methyl-n-butanon-(1)-yl, 2-hydroxycarbonyl2-ethyl-ethanon-(1)-yl, 2-hydroxycarbonyl-2-n-propylethanon-(1)-yl, 2-hydroxycarbonyl-2-ethyl-n-propanon(1)-yl, 3-hydroxycarbonyl-3-ethyl-n-propanon-(1)-yl, 4-hydroxycarbonyl-n-buten-2-on-(1)-yl, 5-hydroxycarbonyl-carbonyl-n-penten-2-on-(1)-yl, methoxycarbonylmethyl, ethoxycarbonylmethyl, isopropoxycarbonylmethyl, 2-methoxycarbonyl-ethyl, 2-ethoxycarbonyl-ethyl, 3-methoxycarbonyl-propyl, 4-ethoxycarbonylbutyl, 2-methoxycarbonyl-1-methyl-ethyl, 2-ethoxycarbonyl1-methyl-ethyl, 2-isopropoxycarbonyl- 1-methyl-ethyl, 1-methoxycarbonyl-ethyl, 1-ethoxycarbonyl- ethyl, 1-methoxycarbonyl-propyl, 1-ethoxycarbonyl-butyl, 1-methoxycarbonyl-1-methyl-ethyl, 1-ethoxycarbonyl-1-methyl-ethyl, 1-isopropoxycarbonyl-1-methyl-ethyl, 2-methoxycarbonyl-ethenyl, 2-methoxycarbonyl-1-methylethenyl, 2-ethoxycarbonyl-1-methyl-ethenyl, 3-methoxycarbonylpropenyl, 2-methoxycarbonyl-ethanon-(1)-yl, 2-(2-methoxyethoxycarbonyl)-ethanon-(1)-yl, 3-methoxycarbonyl-n-propanon-(1)-yl, 3-ethoxycarbonyln-propanon-(1)-yl, 3-(2-ethoxy-ethoxycarbonyl)-n-propanon-(1)-yl, 3-(3-methoxy-n-propoxy-carbonyl)-n-propanon-(1)-yl, 3-n-propoxycarbonyl-n-propanon-(1)-yl, 4-ethoxycarbonyl-n-butanon-(1)-yl, 5-ethoxycarbonyl-npentanon-(1)-yl, 2-ethoxycarbonyl-2-methyl-ethanon-(1)-yl, 3-ethoxycarbonyl-2-methyl-n-propanon-(1)-yl, 3-ethoxycarbonyl-3-methyl-n-propanon-(1)-yl, 4-ethoxycarbonyl-2-methyl-n-butanon-(1)-yl, 4-ethoxycarbonyl-3-methyl-n-butanon-(1)-yl, 4-ethoxycarbonyl-4-methyl-n-butanon-(1)-yl, 2-ethoxycarbonyl-2-ethyl-ethanon-(1)-yl, 2-ethoxycarbonyl-2-n-propyl-ethanon-(1)-yl, 3-ethoxycarbonyl-2ethyl-n-propanon-(1)-yl, 3-ethoxycarbonyl-3-ethyl-n-propanon-(1)-yl, 3-ethoxycarbonyl-n-propanon-(1)-yl, 3-ethoxycarbonyl-2-methyl-n-propanon-(1)-yl, 3-ethoxycarbonyl-3-methyl-n-propanon-(1)-yl, 4-ethoxycarbonyl-n-buten-2-on-(1)-yl, 5-ethoxycarbonyl-n-penten-2-on-(1)-yl, 4,5-dihydro-pyridazin-3-on-6-yl, 4,5-dihydro-5-methyl-pyridazin-3-on-6-yl, 4,5-dihydro5-ethyl-pyridazin-3-on-6-yl, 4,5-dihydro-5-n-propylpyridazin-3-on-6-yl, pyridazin-3-on-6-yl, 5-methylpyridazin-3-on-6-yl, 5-n-propyl-pyridazin-3-on-6-yl or 5-isopropylpyridazin-3-on-6-yl group, and X may represent an oxygen or sulphur atom or an imino, methylimino, ethylimino or isopropylimino group.

The following are examples of compounds which come under general formula I:

methyl 4-[2-(2-(p-chlorobenzenesulphonylamino)-ethyl)-1-methylpyrrol-5-yl]-4-oxybutyrate methyl 4-[2-(2-benzenesulphonylaminoethyl)-1-methylpyrrol-5-yl]-4-oxybutyrate methyl 4-[2-(2-(p-fluorobenzenesulphonylamino)-ethyl)-2-methylpyrrol-5-yl]-4-oxybutyrate methyl 4-[2-(2-benzenesulphonylamino-ethyl)-1-methylpyrrol-5-yl]-4-oxybutyrate methyl 4-[2-(2-thiophen-2-yl-sulphonylamino-ethyl)-1-methylpyrrol-5-yl]-4-oxybutyrate methyl 4-[2-(2-(2,4,5-trichlorobenzenesulphonylamino)ethyl)-1-methyl-pyrrol-5-yl]-4-oxybutyrate methyl 4-[2-(2-(p-toluenesulphonylamino)-ethyl)-1-methylpyrrol-5-yl]-4-oxybutyrate methyl 4-[2-(2-(p-acetamidobenzenesulphonylamino)ethyl)-1-methyl-pyrrol-5-yl]-4-oxybutyrate methyl 4-[2-(2-(p-nitrobenzenesulphonylamino)-ethyl)-1-methyl-pyrrol-5-yl]-4-oxybutyrate methyl 4-[2-(2-(o-methoxybenzenesulphonylamino)-ethyl)-1-methylpyrrol-5-yl]-4-oxybutyrate 4-[2-(2-(p-chlorobenzenesulphonylamino)-ethyl)-1-methylpyrrol-5-yl]-4-oxybutyric acid 4-[2-(2-benzenesulphonylamino-ethyl)-1-methylpyrrol-5-yl]-4-oxybutyric acid 4-[2-(2-(p-fluorobenzenesulphonylamino)-ethyl)-1-methylpyrrol-5-yl]-4-oxybutyric acid 4-[2-(2-benzylsulphonylamino-ethyl)-1-methylpyrrol-5-yl]-4-oxybutyric acid 4-[2-(2-thiophen-2-yl-sulphonylamino-ethyl)-1-methyl-pyrrol-5-yl]-4-oxybutyric acid 4-[2-(2-(2,4,5-trichlorobenzenesulphonylamino)-ethyl)-1-methyl-pyrrol-5-yl]-4-oxybutyric acid 4-[2-(2-(p-toluenesulphonylamino)-ethyl)-1-methylpyrrol-5yl]-4-oxybutyric acid 4-[2-(2-(p-acetamido-benzenesulphonylamino)-ethyl)-1-methylpyrrol-5-yl]-4-oxybutyric acid 4-[2-(2-(p-nitrobenzenesulphonylamino)-ethyl)-1-methylpyrrol-5-yl]-4-oxybutyric acid 4-[2-(2-(2,5-dichlorobenzenesulphonylamino)-ethyl)-1-methylpyrrol-5-yl]-4-oxybutyric acid 4-[2-(2-benzenesulphonylamino-ethyl)-furan-5-yl]-4-oxybutyric acid 4-[2-(2-benzenesulphonylamino-ethyl)-thiophen-5-yl]-4-oxybutyric acid 6-[2-(2-benzenesulphonylamino-ethyl)-1-methylpyrrol-5-yl]4,5-dihydro-3(2H)-pyridazinone 6-[2-(2-(p-fluorobenzenesulphonylamino)-ethyl)-1-methylpyrrol-5-yl]-4,5-dihydro-3(2H) -pyridazinone 6-[2-(2-benzenesulphonylamino-ethyl)-furan-5-yl]-4,5-dihydro-3(2H)-pyridazinone 6-[2-(2-benzenesulphonylamino-ethyl)-thiophen-5-yl]-4,5-dihydro-3(2H)-pyridazinone 4-[2-(2-benzylsulphonylamino-ethyl)-thiophen-5-yl]-4oxybutyric acid methyl [2-(2-(p-chlorobenzenesulphonylamino)-ethyl)-1-methylpyrrol-5-yl]-acetate methyl [2-(2-benzenesulphonylamino-ethyl)-1-methyl-pyrrol-5-yl]-acetate methyl [2-(2-(p-fluorobenzenesulphonylamino)-ethyl)-1-methylpyrrol-5-yl]-acetate methyl [2-(2-thiophen-2-yl-sulphonylamino-ethyl)-1-methylpyrrol-5-yl]-acetate methyl [2-(2-(p-toluenesulphonylamino)-ethyl)-1-methylpyrrol-5-yl]-acetate methyl [2-(2-(p-nitrobenzenesulphonylamino)-ethyl)-1-methylpyrrol-5-yl]-acetate methyl [2-(2-(o-methoxybenzenesulphonylamino)-ethyl)-1-methylpyrrol-5-yl]-acetate

[2-(2-(p-chlorobenzenesulphonylamino)-ethyl)-1-methylpyrrol-5-yl]-acetate acid

[2-(2-benzenesulphonylamino-ethyl)-1-methylpyrrol-5-yl]acetic acid

[2-(2-(p-fluorobenzenesulphonylamino)-ethyl)-1-methylpyrrol-5-yl]-acetic acid

[2-(2-benzylsulphonylamino-ethyl)-1-methylpyrrol-5-yl]acetic acid

[2-(2-thiophen-2-yl-sulphonylamino-ethyl)-1-methylpyrrol-5-yl]-acetic acid

[2-(2-(p-toluenesulphonylamino)-ethyl)-1-methylpyrrol-5-yl]acetic acid

[2-(2-(p-nitrobenzenesulphonylamino)-ethyl)-1-methylpyrrol-5-yl]-acetic acid

[2-(2-(2,5-dichlorobenzenesulphonylamino)-ethyl)-1-methylpyrrol-5-yl]-acetic acid

[2-(2-benzenesulphonylamino-ethyl)-furan-5-yl]-acetic acid

[2-(2-benzenesulphonylamino-ethyl)-thiophen-5-yl]-acetic acid

[2-(2-(p-chlorobenzenesulphonylamino)-ethyl)-thiophen-5-yl]acetic acid

Preferred compounds of general formula I are those wherein $R_1$ represents a phenyl group optionally substituted by a methyl, methoxy or nitro group, or a phenyl group mono-, di- or trisubstituted by a fluorine, chlorine or bromine atom, and $R_2$ represents a hydroxycarbonylmethyl, ethoxycarbonylmethyl, 2-ethoxycarbonyl-ethyl, 3-hydroxycarbonyl-n-propan-(1)-yl, 3-methoxycarbonyl-n-propan-(1)-yl, 3-hydroxycarbonyl-n-propan-1-on-(1)-yl, 3-methoxycarbonyl-n-propan-1-on-(1)-yl or 4,5-dihydropyridazin-3-on-6-yl group, and X represents a methylimino group or an oxygen or sulphur atom.

However, particularly preferred compounds of general formula I above are those wherein $R_1$ represents a phenyl group optionally substituted by a fluorine or chlorine atom or by a methyl or methoxy group, and $R_2$ represents a hydroxycarbonylmethyl, 3-hydroxycarbonyl-n-propan-1-on-(1)-yl or 4,5-dihydro-pyridazin-3-on-6-yl group, and X represents a methylimino group or an oxygen or sulphur atom.

According to the invention the new compounds are obtained by the following methods:

(a) Sulphonylation of a compound of general formula

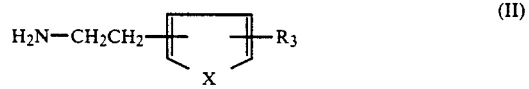

(II)

wherein $R_3$ has the meanings given for $R_2$ hereinbefore, but a hydroxy group in the radical $R_2$ may be protected by a hydrolytically or hydrogenolytically removable protecting group such as an alkoxy or benzyloxy group, with a phenylsulphonic acid derivative of general formula

$R_1—SO_2X$ (III)

wherein $R_1$ is defined as hereinbefore, and

X represents a nucleophilic leaving group such as a halogen atom or an alkoxy group, e.g. a chlorine or bromine atom or a methoxy or ethoxy group, and subsequently any protecting group used is split off.

The reaction is preferably carried out in a solvent such as methanol, ethanol, water/methanol, dioxane, tetrahydrofuran or chloroform, optionally in the presence of an acid binding agent such as potassium carbonate, triethylamine or pyridine, whilst the latter two may also be used as solvent, conveniently at temperatures of between 0° and 50° C. but preferably at ambient temperature.

The subsequent removal of a protecting group, if desired, is preferably carried out hydrolytically in an aqueous solvent, e.g. in water, isopropanol/water, tetrahydrofuran/water or dioxane/water, in the presence of an acid such as hydrochloric or sulphuric acid or in the presence of an alkali metal base such as sodium hydroxide or potassium hydroxide at temperatures between 0° and 100° C., preferably at the boiling temperature of the reaction mixture. However, any benzyl group is preferably split off hydrogenolytically, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures between 0° and 50° C., but preferably at ambient temperature, under a hydrogen pressure of from 1 to 7 bar, preferably 3 to 5 bar.

(b) In order to prepare compounds of general formula I wherein $R_2$ contains a hydroxycarbonyl group:

Splitting off a protecting group from a compound of general formula

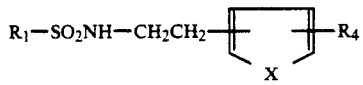

(IV)

wherein $R_1$ is defined as hereinbefore, and $R_4$ has the meanings given for $R_2$ hereinbefore, but the carboxy group is protected by a hydrolytically, thermolytically or hydrogenolytically removable protecting group or constitutes a functional derivative of the carboxy group.

Examples of hydrolysable groups include functional derivatives of the carboxy group, such as the substituted or unsubstituted amides, esters, thioesters, orthoesters, iminoethers, amidines or anhydrides thereof, the nitrile group, ether groups such as the methoxy or benzyloxy group or lactones, and examples of thermolytically removable groups include esters with tertiary alcohols, e.g. the tert.butyl ester, whilst examples of hydrogenolytically removable groups include aralkyl groups, e.g. the benzyl group.

Hydrolysis is appropriately effected either in the presence of an acid such as hydrochloric, sulphuric, phosphoric or trichloroacetic acid or in the presence of a base such as sodium hydroxide or potassium hydroxide in a suitable solvent such as water, water/methanol, ethanol, water/ethanol, water/isopropanol or water/dioxane at temperatures of between −10° and 120° C., e.g. at temperatures of between ambient temperature and the boiling temperature of the reaction mixture.

If, for example, a compound of general formula IV contains a nitrile or aminocarbonyl group, these groups may preferably be converted into the carboxy group using 100% phosphoric acid at temperatures of between 100° and 180° C., preferably at temperatures of between 120° and 160° C., or with a nitrite, e.g. sodium nitrite, in the presence of an acid such as sulphuric acid, which may appropriately also be used as solvent, at temperatures of between 0° and 50° C.

If, for example, a compound of general formula IV contains the tert.butyloxycarbonyl group, the tert.butyl group may also be split off thermally, optionally in an inert solvent such as methylene chloride, chloroform, benzene, toluene, tetrahydrofuran or dioxane and preferably in the presence of a catalytic quantity of an acid such as p-toluenesulphonic acid, sulphuric acid, phosphoric acid or polyphosphoric acid, preferably at the boiling temperature of the solvent used, e.g. at temperatures of between 40° and 100° C.

If, for example, a compound of general formula IV contains the benzyloxy or benzyloxycarbonyl group, the benzyl group may also be split off hydrogenolytically in the presence of a hydrogenation catalyst such as palladium/charcoal in a suitable solvent such as methanol, ethanol, methanol/water, ethanol/water, glacial acetic acid, ethyl acetate, dioxane or dimethylformamide, preferably at temperatures of between 0° and 50° C., e.g. at ambient temperature and under a hydrogen pressure of from 1 to 5 bar. During hydrogenolysis, a halogen-containing compound may simultaneously be dehalogenated and any double bond present may be hydrogenated.

(c) In order to prepare compounds of general formula I wherein $R_2$ contains a carbonyl group adjacent to the heterocyclic group:

Acylating a compound of general formula

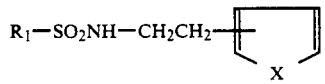

(V)

wherein $R_1$ is as hereinbefore defined, with a compound of general formula $$Y-R_5 \quad (VI)$$

wherein $R_5$ has the meanings given for $R_2$ hereinbefore, but $R_2$ must contain a carbonyl group adjacent to Y and at the same time any hydroxycarbonyl group present may be protected by a hydrolytically or hydrogenolytically removable protecting group such as an alkoxy or benzyl group, and Y represents a nucleophilic leaving group such as a halogen atom, e.g. a chlorine, bromine or iodine atom, or an anhydride thereof in the presence of a Lewis acid, and optionally subsequently splitting off any protecting group used.

Friedel-Crafts acylation is preferably carried out in a solvent such as ethylene chloride or nitrobenzene optionally in the presence of a Lewis acid such as aluminium chloride, boron trifluoride or zinc chloride, appropriately at temperatures of between 0° and 50° C., but preferably at ambient temperature.

The optional subsequent splitting off of a protecting group used is preferably effected by hydrolysis in an aqueous solvent, e.g. in water, isopropanol/water, tetrahydrofuran/water or dioxane/water, in the presence of an acid such as hydrochloric or sulphuric acid or in the presence of an alkali metal base such as sodium hydroxide or potassium hydroxide at temperatures of between 0 and 100° C., preferably at the boiling temperature of the reaction mixture. However, any benzyl group is preferably split off by hydrogenolysis, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures of between 0° and 50° C., but preferably at ambient temperature, under a hydrogen pressure of from 1 to 7 bar, but preferably from 3 to 5 bar.

(d) In order to prepare compounds of general formula I wherein $R_2$ represents a pyridazinone ring:

Reacting a compound of general formula

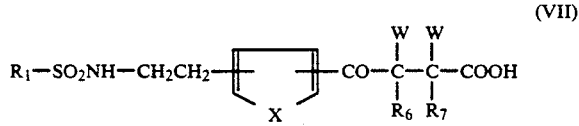
(VII)

wherein $R_1$ is defined as hereinbefore, one of the groups $R_6$ or $R_7$ represents a hydrogen atom or an alkyl group with 1 to 3 carbon atoms and the other group $R_6$ or $R_7$ represents a hydrogen atom, and W represents a hydrogen atom or together they represent another bond, or the reactive derivatives thereof such as the esters, amides or halides thereof, with hydrazine.

The reaction is appropriately carried out in a solvent such as methanol, ethanol, isopropanol, glacial acetic acid, propionic acid and/or in an excess of hydrazine or hydrazine hydrate at temperatures of between 0° and 200° C., e.g. at temperatures of between 20° and 150° C., but preferably at the boiling temperature of the reaction mixture, and optionally in the presence of an acid as condensing agent, such as sulphuric acid or p-toluenesulphonic acid. However, the reaction may also be carried out without a solvent.

(e) In order to prepare compounds of general formula I wherein $R_2$ represents a hydroxycarbonyl or alkoxycarbonyl group bonded via a methylene group:

Reacting a compound of general formula

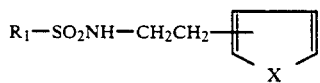
(VIII)

wherein $R_1$ and X are defined as hereinbefore, with a diazoacetic acid ester of general formula $$N_2CH-COOR_8 \quad (IX)$$

wherein $R_8$ represents an alkyl group with 1 to 3 carbon atoms, optionally with subsequent hydrolysis.

The reaction is preferably carried out in a suitable solvent such as ethylene chloride, tetrahydrofuran or dioxane, conveniently under a protective gas and in the presence of a metal such as copper powder or a heavy metal salt such as copper(I) chloride or copper(II) chloride at temperatures of between 25° and 100° C., preferably at the boiling temperature of the reaction mixture. The subsequent hydrolysis is preferably carried out in an aqueous solvent, e.g. in water, isopropanol/water, tetrahydrofuran/water or dioxane/water, in the presence of an acid such as hydrochloric or sulphuric acid or in the presence of an alkali metal base such as sodium hydroxide or potassium hydroxide at temperatures of between 0° and 100° C., preferably at the boiling temperature of the reaction mixture.

If according to the invention a compound of general formula I is obtained wherein $R_2$ contains a hydroxycarbonyl group, this may be converted into a corresponding alkoxycarbonyl compound by esterification.

The subsequent esterification is conveniently carried out in a solvent, e.g. an excess of the alcohol used such as methanol, ethanol or isopropanol, in the presence of an acid activating agent such as thionyl chloride or hydrogen chloride gas at temperatures of between 0° and 180° C., but preferably at the boiling temperature of the reaction mixture.

If $R_2$ contains an optically active carbon atom, the compounds of general formula I obtained may also be resolved into their enantiomers. Thus, the compounds of general formula I obtained which contain only one optically active center may be resolved into their optical enantiomers by methods known per se (see Alinger N. L. and Elich W. L. in "Topics in Stereochemistry", Vol. 6, Wiley Interscience, 1971), e.g. by recrystallisation from an optically active solvent or by reaction with an optically active substance which forms salts with the racemic compound, particularly a base, and separating the salt mixture thus obtained, e.g. on the basis of different solubilities, into the diastereomeric salts from which the free enantiomers can be liberated by the use of suitable agents. Particularly common optically active bases include, for example, the D- and L- forms of α-phenylethylamine or cinchonidine.

Moreover, the new compounds of general formula I obtained, if they contain a carboxy group, may, if desired, subsequently be converted into the addition salts thereof with inorganic or organic bases, more particularly into the physiologically acceptable addition salts thereof for pharmaceutical use. Bases which might be used include, for example, sodium hydroxide, potassium hydroxide, cyclohexylamine, ethanolamine, diethanolamine and triethanolamine.

As already mentioned hereinbefore, the new compounds and the physiologically acceptable addition salts thereof with inorganic or organic bases have valuable pharmacological properties, particularly antithrombotic activities and an inhibiting effect on platelet aggregation. They are also thromboxane antagonists. The pyridazinones of general formula I, because of their inhibiting effect on phosphodiesterase, also exhibit an inhibiting effect on tumour metastasis.

For example, the new compounds

A = 4-[2-(2-benzenesulphonylamino-ethyl)-1-methylpyrrol-5yl]-4-oxybutyric acid,

B = 4-[2-(2-(p-chlorobenzenesulphonylamino)-ethyl)-1-methylpyrrol-5-yl]-4-oxybutyric acid, C = 4-[2-(2-thiophen-2-yl-sulphonylamino-ethyl)-1-methylpyrrol-5-yl]-4-oxybutyric acid, D = 4-[2-(2-(p-fluorobenzenesulphonylamino)-ethyl)-1methylpyrrol-5-yl]-4-oxybutyric acid, and E = 6-[2-(2-benzenesulphonylamino-ethyl)-1-methylpyrrol5-yl]-4,5-dihydro-3(2H)-pyridazinone were tested for their biological properties as follows:

1. Antithrombotic activity

Procedure

Thrombocyte aggregation is measured using the BORN and CROSS method (J. Physiol. 170, 397 (1964)) in the platelet-rich plasma of healthy test subjects. To inhibit coagulation, 3.14% sodium citrate is added to the blood in a ratio by volume of 1:10.

Collagen-induced aggregation

The pattern of the decrease in optical density of the platelet suspension is photometrically measured and recorded after the addition of aggregation-inducing substance. The rate of aggregation is determined from the angle of inclination of the density curve. The point on the curve at which there is maximum transmittance is used to calculate the "optical density".

The quantity of collagen is kept as small as possible but sufficient to produce an irreversible reaction curve. The standard commercial collagen produced by Hormonchemie of Munich is used. Before the addition of collagen, the plasma is incubated for 10 minutes with the substance at 37° C.

From the measurements obtained, an $EC_{50}$ is determined graphically, showing a 50% change in the "optical density" in terms of an inhibition of aggregation.

The following Table contains the results found:

| Substance | $EC_{50}$ [Mol/l] |
|---|---|
| A | $3.5 \times 10^{-6}$ |
| B | $4.0 \times 10^{-7}$ |
| C | $3.9 \times 10^{-7}$ |
| D | $3.6 \times 10^{-7}$ |
| E | $2.9 \times 10^{-6}$ |

2. Acute toxicity

The acute toxicity of the substances being tested was determined approximately in groups of 10 mice after oral administration of a single dose (observation period 14 days):

| Substance | Approximate acute toxicity |
|---|---|
| A | 500 mg/kg (0 out of 10 animals died) |
| B | 500 mg/kg (0 out of 10 animals died) |
| C | 500 mg/kg (0 out of 10 animals died) |
| D | 500 mg/kg (0 out of 10 animals died) |
| E | 500 mg/kg (0 out of 10 animals died) |

In view of their pharmacological properties, the new compounds and their physiologically acceptable addition salts are suitable for the treatment and prophylaxis of thrombo-embolic disorders such as coronary infarction, cerebral infarction, so-called transient ischaemic attacks and amaurosis fugax, and for the prophylaxis of arteriosclerosis and metastasis.

The dosage required to obtain such an activity is approximately 0.3 to 4 mg/kg of body weight, preferably 0.3 to 2 mg/kg of body weight, 2 to 4 times a day. For this purpose, the compounds of general formula I prepared according to the invention, possibly combined with other active substances, may be processed with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethyl cellulose or fatty substances such as hard fat or suitable mixtures thereof, to produce conventional galenic preparations such as plain or coated tablets, capsules, powders, suspensions or suppositories.

The present invention further relates to the new intermediate products of general formula $$R_1-SO_2NH-CH_2CH_2-\text{[ring with } X_1\text{]} \quad (X)$$

wherein
$R_1$ is defined as hereinbefore, and
$X_1$ represents an imino group optionally substituted by an alkyl group with 1 to 3 carbon atoms, or an oxygen atom.

The new compounds of general formula VIII are obtained by acylating a compound of general formula $$H_2N-CH_2CH_2-\text{[ring with } X_1\text{]} \quad (XI)$$

wherein
$X_1$ is defined as hereinbefore, with a phenylsulphonic acid derivative of general formula $$R_1-SO_2X \quad (III)$$

wherein
$R_1$ is defined as hereinbefore, and
X represents a nucleophilic leaving group such as a halogen atom or alkoxy group, e.g. a chlorine or bromine atom or a methoxy or ethoxy group.

The reaction is preferably carried out in a solvent such as methanol, ethanol, water/methanol, dioxane, tetrahydrofuran or chloroform, optionally in the presence of an acid binding agent such as potassium carbonate, triethylamine or pyridine, whilst the latter two may also be used as solvents, conveniently at temperatures of between 0° and 50° C., but preferably at ambient temperature.

The compounds of general formulae II to XI used as starting materials are obtained by methods known from the literature or are already known in the literature.

A compound of general formula II used as starting material is obtained from a corresponding N-acylaminoethyl compound by Friedel-Crafts acylation, subsequent deacylation and, if desired, subsequent reduction, hydrolysis and/or esterification.

The compounds of general formulae IV, V, VII and VIII used as starting materials are obtained by reacting a corresponding amino compound with a corresponding sulphonyl halide.

The Examples which follow are intended to illustrate the invention:

EXAMPLE A

2-[2-(p-ChlorobenzenesulphonYlamino)-ethyl]-1-methylpyrrole 10 ml of a saturated potassium carbonate solution are added to a solution of 4.96 g of 2-(2-aminoethyl)-1-methylpyrrole in 20 ml of dioxane, with stirring. Then at 0° C. a solution of 10.1 g of p-chlorobenzene sulphonylchloride in 30 ml of dioxane is added dropwise. The mixture is then stirred for 3 hours at ambient temperature, the precipitate is removed by suction filtering, washed with ether and the organic phase is separated off. After drying over sodium sulphate 10 g of crude product are obtained which is chromatographed over a silica gel column with methylene chloride/cyclohexane (9:1).
Yield: 6.6 g (55% of theory),
Melting point: 73°–75° C.

| $C_{13}H_{15}ClN_2O_2S$ (298.81) | | | |
|---|---|---|---|
| Calculated: | C 52.25 | H 5.05 | N 9.38 |
| Found: | 52.70 | 4.95 | 9.16 |

EXAMPLE B 2-(2-Benzenesulphonylamino-ethyl)-1-methylpyrrole

Prepared from 2-(2-aminoethyl)-1-methylpyrrole and benzenesulphonyl chloride analogously to Example A.
Yield: 76% of theory,
Melting point: 63°–65° C.

| $C_{13}H_{16}N_2O_2S$ (264.4) | | | |
|---|---|---|---|
| Calculated: | C 59.07 | H 6.10 | N 10.60 |
| Found: | 59.22 | 6.97 | 10.62 |

EXAMPLE C

2-[2-(p-Fluorobenzenesulphonylamino)-ethyl]-1-methylpyrrole

Prepared from 2-(2-aminoethyl)-1-methylpyrrole and p-fluorobenzenesulphonylchloride analogously to Example A.
Yield: 89% of theory,
Melting Point: 92°–95° C.

| $C_{13}H_{15}FN_2O_2S$ (282.35) | | | |
|---|---|---|---|
| Calculated: | C 55.30 | H 5.35 | N 9.92 |
| Found: | 55.15 | 5.05 | 9.84 |

EXAMPLE D 2-(2-Benzylsulphonylamino-ethyl)-1-methylpyrrole

Prepared from 2-(2-aminoethyl)-1-methylpyrrole and benzylsulphonyl chloride analogously to Example A.
Yield: 74% of theory,
Melting Point: 91°–93° C.

| $C_{14}H_{18}N_2O_2S$ (278.4) | | | |
|---|---|---|---|
| Calculated: | C 60.41 | H 6.52 | N 10.07 |
| Found: | 60.70 | 6.72 | 10.15 |

EXAMPLE E

2-[2-(2-Thienylsulphonylamino)-ethyl]-1-methylpyrrole

Prepared from 2-(2-aminoethyl)-1-methylpyrrole and 2-thienylsulphonylchloride analogously to Example A.
Yield: 89% of theory,
Melting Point: 63°–65° C.

| $C_{11}H_{14}N_2O_2S_2$ (270.38) | | | |
|---|---|---|---|
| Calculated: | C 48.87 | H 5.22 | N 10.36 |
| Found: | 49.62 | 5.13 | 10.30 |

EXAMPLE F

2-[2-(2,4,5-Trichlorobenzenesulphonylamino)-ethyl]-1methylpyrrole

Prepared from 2-(2-aminoethyl)-1-methylpyrrole and 2,4,5-trichlorobenzenesulphonylchloride analogously to Example A.
Yield: 88% of theory,
Melting point: 87°–90° C.

| $C_{13}H_{13}Cl_3N_2O_2S$ (367.7) | | | |
|---|---|---|---|
| Calculated: | C 42.46 | H 3.56 | N 7.62 |
| Found: | 43.10 | 3.65 | 7.46 |

EXAMPLE G

2-[2-(p-Toluenesulphonylamino)-ethyl]-1-methylpyrrole

Prepared from 2-(2-aminoethyl)-1-methylpyrrole and p-toluenesulphonylchloride analogously to Example A.
Yield: 73% of theory,
Melting point: 63°–65° C.

| $C_{14}H_{18}N_2O_2S$ (278.4) | | | |
|---|---|---|---|
| Calculated: | C 60.39 | H 6.51 | N 10.06 |
| Found: | 60.40 | 6.65 | 9.91 |

EXAMPLE H

2-[2-(p-Acetamidobenzenesulphonylamino)-ethyl]-1-methylpyrrole Prepared from 2-(2-aminoethyl)-1-methylpyrrole and p-acetamidobenzenesulphonylchloride analogously to Example A.
Yield: 80% of theory,
Melting point: 123°–125° C.

| $C_{15}H_{19}N_3O_3S$ (321.4) | | | |
|---|---|---|---|
| Calculated: | C 56.05 | H 5.95 | N 13.07 |
| Found: | 55.87 | 5.87 | 12.35 |

EXAMPLE I

2]2-(p-Nitrobenzenesulphonylamino)-ethyl]-1-methylpyrrole

Prepared from 2-(2-aminoethyl)-1-methylpyrrole and p-nitrobenzenesulphonylchloride analogously to Example A.
Yield: 78% of theory,
Melting point: 102° C.

| $C_{13}H_{15}O_4N_3S$ (309.35) | | | |
|---|---|---|---|
| Calculated: | C 50.46 | H 4.88 | N 13.59 |
| Found: | 50.60 | 4.86 | 13.54 |

EXAMPLE K

2-[2-(2-Methoxybenzenesulphonylamino)-ethyl]-1-methylpyrrole

Prepared from 2-(2-aminoethyl)-1-methylpyrrole and 2-methoxybenzenesulphonylchloride analogously to Example A.

Yield: 75% of theory,
Melting point: oil

| C$_{14}$H$_{18}$O$_3$N$_2$S (294.3) | | | |
|---|---|---|---|
| Calculated: | C 57.13 | H 6.16 | N 9.51 |
| Found: | 56.41 | 6.10 | 9.10 |

EXAMPLE L

2-[2-(2,5-Dichlorobenzenesulphonylamino)-ethyl]-1methylpyrrole

Prepared from 2-(2-aminoethyl)-1-methylpyrrole and 2,5-dichlorobenzenesulphonylchloride analogously to Example A.
Yield: 60% of theory,
Melting point: 84°–86° C.

| C$_{13}$H$_{14}$Cl$_2$N$_2$O$_2$S (333.25) | | | |
|---|---|---|---|
| Calculated: | C 46.85 | H 4.24 | N 8.41 |
| Found: | 46.84 | 4.26 | 8.54 |

EXAMPLE M 2-(2-Benzenesulphonylamino-ethyl)-furan 3.2 g of 2-(2-aminoethyl)-furan are dissolved in 45 ml of pyridine and at 5° C. a solution of 8.8 g of benzenesulphonic acid chloride in 50 ml of pyridine is added. The resulting mixture is then stirred overnight at ambient temperature, the reaction product is evaporated down, the residue is taken up in water and extracted with methylene chloride. After the organic phase has been dried over magnesium sulphate the solution is concentrated by evaporation and chromatographed over a silica gel column using ethylene chloride.
Yield: 78% of theory,
Melting point: resinous product

| C$_{12}$H$_{13}$NO$_3$S (251.31) | | | |
|---|---|---|---|
| Calculated: | C 57.35 | H 5.21 | N 5.58 |
| Found: | 57.53 | 5.20 | 5.76 |

EXAMPLE 1

Methyl 4-[2-(2-(p-chlorobenzenesulphonylamino)ethyl)-1-methylpyrrol-5-yl]-4-oxybutyrate 2.7 g of carbomethoxypropionyl chloride are added to a solution of 3.9 g of 2-[2-(p-chlorobenzenesulphonylamino)-ethyl]-1-methylpyrrole in 35 ml of dry ethylene chloride and the mixture is stirred for 3 hours at 60° C. The solution is then evaporated down and the residue is chromatographed over a silica gel column with chloroform/ethyl acetate (7:3).
Yield: 45% of theory,
Melting point: sinters from 60° C.

| C$_{18}$H$_{21}$ClN$_2$O$_5$S (412.92) | | | |
|---|---|---|---|
| Calculated: | C 52.37 | H 5.13 | Cl 8.58 |
| Found: | 53.64 | 5.68 | 8.25 |

EXAMPLE 2

Methyl 4-[2-(2-benzenesulphonylamino-ethyl)-1-methylpyrrol-5-yl]-4-oxybutyrate

Prepared from 2-(2-benzenesulphonylaminoethyl)1-methylpyrrole and carbomethoxypropionyl chloride analogously to Example 1.
Yield: 43% of theory,
Melting point: 89°–91° C.

| C$_{18}$H$_{22}$N$_2$O$_5$S (378.47) | | | |
|---|---|---|---|
| Calculated: | C 57.13 | H 5.86 | N 7.40 |
| Found: | 57.11 | 5.73 | 7.30 |

EXAMPLE 3

Methyl 4-[2-(2-(p-fluorobenzenesulphonylamino)ethyl)-1-methylpyrrol-5-yl]-4-oxybutyrate Prepared from 2-[2-(p-fluorobenzenesulphonylamino)ethyl]-1-methylpyrrole and carbomethoxy propionyl chloride analogously to Example 1.
Melting point: 85°–88° C.

| C$_{18}$H$_{21}$FN$_2$O$_5$S (396.46) | | | |
|---|---|---|---|
| Calculated: | C 54.54 | H 5.34 | N 7.07 |
| Found: | 54.30 | 5.20 | 7.19 |

EXAMPLE 4

Methyl 4-[2-(2-benzenesulphonylamino-ethyl)-1-methylpyrrol-5-yl]-4-oxybutyrate

Prepared from 2-(2-benzenesulphonylamino-ethyl)-1methylpyrrole and carbomethoxypropionyl chloride analogously to Example 1.
Yield: 34% of theory,
Melting point: resinous product

| C$_{19}$H$_{24}$N$_2$O$_2$S (392.49) | | | |
|---|---|---|---|
| Calculated: | C 58.14 | H 6.16 | S 8.17 |
| Found: | 58.00 | 6.07 | 8.08 |

EXAMPLE 5

Methyl 4-[2-(2-thiophen-2-yl-sulphonylamino-ethyl)1-methyl-pyrrole-5-yl]-4-oxybutyrate Prepared from 2-(2-thiophen-2-yl-sulphonylaminoethyl)1-methylpyrrole and carbomethoxypropionyl chloride analogously to Example 1.
Yield: 40% of theory,
Melting point: resinous product

| C$_{16}$H$_{20}$N$_2$O$_5$S$_2$ (384.49) | | | |
|---|---|---|---|
| Calculated: | C 49.98 | H 5.24 | N 7.29 |
| Found: | 49.74 | 5.39 | 7.55 |

Example 6

Methyl 4-[2-(2-(2,4,5-trichlorobenzenesulphonylamino)-ethyl)-1-methylpyrrol-5-yl]-4-oxybutyrate Prepared from 2-[2-(2,4,5-trichlorobenzenesulphonylamino)-ethyl]-1-methylpyrrole and carbomethoxypropionyl chloride analoqously to Example 1.
Yield: 57% of theory,
Melting point: resinous product

| $C_{18}H_{19}Cl_3N_2O_5S$ (481.81) | | | |
|---|---|---|---|
| Calculated: | C 44.88 | H 3.95 | S 6.65 |
| Found | 45.12 | 4.34 | 6.81 |

EXAMPLE 7

Methyl 4-[2-(2-(p-toluenesulphonylamino)-ethyl)-1-methylpyrrol-5-yl]-4-oxybutyrate Prepared from 2-[2-(p-toluenesulphonylamino)-ethyl]-1-methylpyrrole and carbomethoxypropionyl chloride analogously to Example 1.
Yield: 35% of theory

| $C_{19}H_{17}O_5N_2S$ (385.42) | | | |
|---|---|---|---|
| Calculated: | C 59.21 | H 4.44 | S 8.32 |
| Found: | 59.66 | 5.07 | 8.84 |

EXAMPLE 8

Methyl 4-[2-(2-(p-acetamidobenzenesulphonylamino)-ethyl)-1-methylpyrrol-5-yl]-4-oxybutyrate Prepared from 2-[2-(p-acetamidobenzenesulphonylamino)ethyl]-1-methylpyrrole and carbomethoxypropionyl chloride analogously to Example 1.
Yield: 8% of theory,
Melting point: 130°–131° C.

| $C_{20}H_{22}N_3O_6S$ (435.5) | | | |
|---|---|---|---|
| Calculated: | C 55.15 | H 5.78 | S 7.36 |
| Found: | 56.48 | 5.52 | 7.48 |

EXAMPLE 9

Methyl 4-[2-(2-(p-nitrobenzenesulphonylamino)-ethyl)1-methylpyrrol-5-yl]-4-oxybutyrate Prepared from 2-(2-(p-nitrobenzenesulphonylamino)ethyl]-1-methylpyrrole and carbomethoxypropionyl chloride analogously to Example 1.
118°–120° C.

| $C_{18}H_{21}N_3O_7S$ (423.4) | | | |
|---|---|---|---|
| Calculated: | C 51.06 | H 4.99 | N 9.92 |
| Found: | 50.80 | 4.96 | 9.97 |

EXAMPLE 10

Methyl 4-[2-(2-(o-methoxybenzenesulphonylamino)ethyl)-1-methylpyrrol-5-yl]-4-oxybutyrate Prepared from 2-[2-(o-methoxybenzenesulphonylamino)ethyl]-1-methylpyrrole and carbomethoxypropionyl chloride analogously to Example 1.
Yield: 53% of theory,
Melting point: resin

| $C_{19}H_{24}N_2O_6S$ (380.5) | | | |
|---|---|---|---|
| Calculated: | C 55.86 | H 5.92 | N 6.85 |
| Found: | 56.40 | 5.98 | 6.67 |

EXAMPLE 11

4-[2-(2-(p-Chlorobenzenesulphonylamino)-ethyl)-1-methylpyrrol-5-yl]-4-oxybutyric acid 1.03 g of methyl 4-[2-(2-(p-chlorobenzenesulphonylamino)-ethyl)-1-methylpyrrol-5-yl]-4-oxybutyrate are added to 15 ml of 1N sodium hydroxide solution and stirred for 3 hours at 50° C. The solution is then made acidic with 8 ml of 2N hydrochloric acid and the precipitate is suction filtered.
Yield: 0.5 g (50% of theory),
Melting point: 127°–130° C.

| $C_{17}H_{19}ClN_2O_5S$ (398.89) | | | |
|---|---|---|---|
| Calculated: | C 51.18 | H 4.80 | N 7.03 |
| Found: | 51.20 | 4.36 | 6.90 |

EXAMPLE 12

4-[2-(2-Benzenesulphonylamino-ethyl)-1-methylpyrrol-5-yl]-4-oxybutyric acid

Prepared from methyl 4-[2-(2-benzenesulphonylaminoethyl)-1-methylpyrrol-5-yl]-4-oxybutyrate analogously to Example 11.
Yield: 77% of theory,
Melting point: 120°–122° C.

| $C_{17}H_{20}N_2O_5S$ (364.4) | | | |
|---|---|---|---|
| Calculated: | C 56.03 | H 5.53 | N 7.69 |
| Found: | 55.90 | 5.33 | 7.43 |

EXAMPLE 13

4-[2-(2-(p-Fluorobenzenesulphonylamino)-ethyl)-1-methylpyrrol-5-yl]-4-oxybutyric acid Prepared from methyl 4-[2-(2-(p-fluorobenzenesulphonylamino)-ethyl)-1-methylpyrrol-5-yl]-4-oxybutyrate analogously to Example 11.
Yield: 92% of theory,
Melting point: 142°–143° C.

| $C_{17}H_{19}FN_2O_5S$ (382.43) | | | |
|---|---|---|---|
| Calculated: | C 53.39 | H 5.01 | N 7.32 |
| Found | 53.57 | 4.92 | 6.86 |

EXAMPLE 14

4-[2-(2-Benzylsulphonylamino)-1-methylpyrrol-5-yl]-4-oxybutyric acid

Prepared from methyl 4-[2-(2-benzylsulphonylaminoethyl)-1-methylpyrrol-5-yl]-4-oxybutyrate analogously to Example 11.
Yield: 70% of theory,
melting Point: 156°–159° C.

| $C_{18}H_{22}N_2O_5S$ (378.47) | | | |
|---|---|---|---|
| Calculated: | C 57.13 | H 5.86 | N 7.40 |
| Found: | 57.20 | 5.72 | 7.11 |

Example 15

4-[2-(2-Thiophen-2-yl-sulphonylamino-ethyl)-1-methylpyrrol-5-yl]-4-oxybutyric acid Prepared from methyl 4-[2-(2-thiophen-2-yl-sulphonylamino-ethyl-1-methylpyrrol-5-yl]-4-oxybutyrate analogously to Example 11.
Yield: 41% of theory,
Melting point: 135°–137° C.

| $C_{15}H_{18}N_2O_5S_2$ (370.46) | | | |
|---|---|---|---|
| Calculated: | C 48.63 | H 4.90 | N 7.56 |
| Found: | 48.36 | 4.83 | 7.60 |

EXAMPLE 16

4-[2-(2-(2,4,5-Trichlorobenzenesulphonylamino)-ethyl)-1-methylpyrrol-5-yl]-4-oxybutyric acid Prepared from methyl 4-[2-(2-(2,4,5-trichlorobenzenesulphonylamino)-ethyl)-1-methylpyrrol-5-yl]-4-oxybutyrate analogously to Example 11.
Yield: 78% of theory,
Melting point: 152°–155° C.

| $C_{17}H_{17}Cl_3N_2O_5S$ (467.79) | | | |
|---|---|---|---|
| Calculated: | C 43.65 | H 3.66 | N 5.99 |
| Found: | 43.42 | 3.42 | 5.98 |

EXAMPLE 17

4-[2-(2-(p-Toluenesulphonylamino)-ethyl)-1-methylpyrrol-5-yl]-4-oxybutyric acid

Prepared from methyl 4-[2-(2-(p-toluenesulphonylamino)ethyl)-1-methylpyrrol-5-yl]-4-oxybutyrate analogously to Example 11.
Yield: 86% of theory,
Melting point: 195°–198° C.

| $C_{18}H_{22}N_2O_5S$ (378.5) | | | |
|---|---|---|---|
| Calculated: | C 57.13 | H 5.86 | N 7.40 |
| Found: | 57.20 | 5.87 | 7.36 |

EXAMPLE 18

4-[2-(2-(p-Acetamido-benzenesulphonylamino)-ethyl)-1-methylpyrrol-5-yl]-4-oxybutyric acid Prepared from methyl 4-[2-(2-(p-acetamido-benzenesulphonylamino)-ethyl)-1-methylpyrrol-5-yl]-4-oxybutyrate analogously to Example 11.
Yield: 24% of theory,
Melting point: 124°–126° C.

| $C_{19}H_{23}N_3O_6S$ (421.5) | | | |
|---|---|---|---|
| Calculated: | C 54.14 | H 5.50 | N 9.97 |
| Found: | 53.03 | 5.50 | 10.62 |

EXAMPLE 19

4-[2-(2-(p-Nitrobenzenesulphonylamino)-ethyl)-1-methylpyrrol-5-yl]-4-oxybutyric acid Prepared from methyl 4-[2-(2-(p-nitrobenzenesulphonylamino)-ethyl)-1-methylpyrrol-5-yl]-4-oxybutyrate analogously to Example 11.
Yield: 55% of theory,
Melting point: 181° C.

| $C_{17}H_{19}N_3O_7S$ (409.4) | | | |
|---|---|---|---|
| Calculated: | C 49.87 | H 4.68 | N 10.26 |
| Found: | 49.50 | 4.55 | 10.33 |

EXAMPLE 20

4-[2-(2-(2,5-Dichlorobenzenesulphonylamino)-ethyl)-1-methylpyrrol-5-yl]-4-oxybutyric acid At $-5°$ C., 1.1 g of succinic acid anhydride in 50 ml of ethylene chloride are added to a suspension of 2.7 g of aluminium chloride in 20 ml of dry ethylene chloride. Then 3.3 g of 2-[2-(2,5-dichlorobenzenesulphonylamino)-ethyl]-1-methylpyrrole in 25 ml of ethylene chloride are added and the mixture is stirred for 3 hours at ambient temperature. Ice water is then added, the organic phase is separated off, extracted with 2% sodium hydroxide solution and the aqueous phase is acidified. The resinous product precipitated is collected.
Yield: 0.6 g (14% of theory),
Melting Point: resin

| $C_{17}H_{18}Cl_2N_2O_5S$ | | | | | |
|---|---|---|---|---|---|
| Calculated | C | 47.12 | H | 4.19 | Cl 16.37 |
| Found | | 47.40 | | 4.29 | 16.63 |

EXAMPLE 21

4-[2-(2-Benzenesulphonylamino-ethyl)-furan-5-yl]-4-oxybutyric acid

Prepared from 2-(2-benzenesulphonylamino-ethyl)-furan and succinic acid anhydride analogously to Example 20.
Yield: 65% of theory,
Melting Point: 126°–129° C.

| $C_{16}H_{17}NO_6S$ (351.40) | | | |
|---|---|---|---|
| Calculated | C 54.69 | H 4.88 | N 3.99 |

-continued

| | C₁₆H₁₇NO₆S (351.40) | | |
|---|---|---|---|
| Found | 54.77 | 4.69 | 3.92 |

EXAMPLE 22

4-[2-(2-Benzenesulphonylamino-ethyl)-thiophen-5-yl]-4-oxybutyric acid

Prepared from 2-(2-benzenesulphonylamino-ethyl)-thiophene and succinic acid anhydride analogously to Example 20.
Yield: 62% of theory,
Melting point: 140°–142° C.

| | C₁₆H₁₇NO₃S₂(367.5) | | | |
|---|---|---|---|---|
| Calculated | C | 52.30 | H 4.66 | N 3.81 |
| Found | | 52.36 | 4.79 | 3.86 |

EXAMPLE 23

6-[2-(2-Benzenesulphonylamino-ethyl)-1-methylpyrrol-5-yl]-4,5-dihydro-3(2H)-pyridazinone 1.46 g of 4-[2-(2-benzenesulphonylamino-ethyl)-1-methylpyrrol-5-yl]-4-oxybutyric acid are suspended in 10 ml of glacial acetic acid, 2.2 g of hydrazine hydrate are added and the mixture is refluxed for 6 hours. The solution is then evaporated down, the reaction product is mixed with water and made basic with 2N ammonia. The precipitate obtained is dissolved in hot methanol, filtered off from the insoluble precipitate and evaporated down.
Yield: 0.72 g (50% of theory),
Melting point: 180°–182° C.

| | C₁₇H₂₀N₄O₃S (360.4) | | | |
|---|---|---|---|---|
| Calculated | C 56.65 | H 5.59 | N 15.54 | |
| Found: | 56.33 | 5.52 | 15.75 | |

EXAMPLE 24

6-[2-(2-(p-Fluorobenzenesulphonylamino)-ethyl)-1-methylpyrrol-5-yl]-4,5-dihydro-3(2H)-pyridazinone Prepared from 4-[2-(2-(p-fluorobenzenesulphonylamino)-ethyl)-1-methylpyrrol-5-yl]-4-oxybutyric acid and hydrazine hydrate analogously to Example 23.
Yield: 29% of theory,
Melting point: 201° C.

| | C₁₇H₁₉N₄O₃FS (378.4) | | | |
|---|---|---|---|---|
| Calculated: | C 53.96 | H 5.06 | N 14.86 | |
| Found | 53.74 | 5.35 | 14.10 | |

EXAMPLE 25

6-[2-(2-Benzenesulphonylamino-ethyl)-furan-5-yl]-4,5-dihydro-3(2H)-pyridazinone

Prepared from 4-[2-(2-benzenesulphonylamino-ethyl)furan-5-yl]-4-oxybutyric acid and hydrazine hydrate analogously to Example 23.
Yield: 85% of theory,
Melting point: 174°–176° C.

| | C₁₆H₁₇N₃O₄S (347.4) | | | |
|---|---|---|---|---|
| Calculated | C 55.31 | H 4.93 | N 12.09 | |
| Found | 55.20 | 5.06 | 12.36 | |

EXAMPLE 26

6-[2-(2-Benzenesulphonylamino-ethyl)-thiophen-5-yl]-4,5-dihydro-3(2H)-pyridazinone Prepared from 4-[2-(2-benzenesulphonylamino-ethyl)thiophen-5-yl]-4-oxybutyric acid and hydrazine hydrate analogously to Example 23.
Yield: 64% of theory,
Melting point: 140° C.

| | C₁₅H₁₇N₃O₂S₂(351.5) | | | |
|---|---|---|---|---|
| Calculated | C 51.25 | H 4.87 | N 11.95 | |
| Found | 51.71 | 4.71 | 11.78 | |

EXAMPLE 27

4-[2-(2-Benzylsulphonylamino-ethyl)-thiophen-5-yl]-4-oxybutyric acid (a) 4-[2-(2-Acetylamino-ethyl)-thiophen-5-yl]-4-oxybutyric acid Prepared analogously to Example 23 from 2-(2-acetylamino-ethyl)-thiophene and succinic acid anhydride.
Yield: 41% of theory,
Melting point: 116°–118° C.

| | C₁₂H₁₅NO₄S (269.3) | | | |
|---|---|---|---|---|
| Calculated | C 53.26 | H 5.61 | N 11.91 | |
| Found | 53.24 | 5.61 | 12.03 | |

(b) Methyl 4-[2-(2-amino-ethyl)-thiophen-5-yl]-4-oxybutyrate hydrochloride 1.0 g of 4-(2-(2-acetylamino-ethyl)-thiophen-5-yl)-4-oxybutyric acid are refluxed overnight in 15 ml of conc. hydrochloric acid and 10 ml of methanol. The solution is then concentrated by evaporation and the residue is dried.
Yield: 0.6 g (57% of theory),
Melting Point: 153°–155° C.

(c) 4-[2-(2-Benzylsulphonylamino-ethyl)-thiophen-5-yl]-4-oxybutyric acid 0.6 g of methyl 4-(2-(2-amino-ethyl)-thiophen-5-yl]-4-oxybutyrate are dissolved in 30 ml of pyridine and at 0° C. 0.95 g of benzylsulphonic acid chloride dissolved in 20 ml of pyridine are added. The mixture is then stirred for 3 hours at ambient temperature, the pyridine is separated off in vacuo, the residue is mixed with water and the product is extracted with methylene chloride. The combined organic phases are dried with sodium sulphate and concentrated by rotary evaporation. The resinous residue obtained is stirred with 20 ml of 1N sodium hydroxide solution for 2 hours at 70° C. This solution is filtered and acidified, whereupon the product is precipitated.
Yield: 150 mg (20% of theory), Melting point: 112°–115° C.

| C₁₇H₁₉NO₅S₂ (381.5) | | | | | | | | |
|---|---|---|---|---|---|---|---|---|
| Calculated | C | 53.52 | H | 5.02 | N | 3.67 | S | 16.81 |
| Found | | 53.13 | | 4.80 | | 3.28 | | 16.74 |

EXAMPLE 28

Ethyl [2-(2-(4-fluorobenzenesulphonylamino)-ethyl)-1-methylpyrrol-5-yl]-acetate 1.69 g of 2-(2-(4-fluorobenzenesulphonylamino)-ethyl)-1-methylpyrrole are dissolved in 6 ml of ethylene chloride and 0.06 g of copper(I)chloride are added. Under a nitrogen atmosphere the mixture is refluxed and then a solution of 0.34 g of ethyl diazoacetate in 6 ml of ethylene chloride is slowly added dropwise. After 20 minutes the evolution of nitrogen has ended and the suspension is concentrated to dryness by rotary evaporation. Then the residue is chromatographed over a silica gel column (ethylene chloride/ethyl acetate = 100/1).

Yield: 0.7 g (63% of theory) resin,

| C₁₇H₂₁FN₂O₄S (368.4) | | | | | | | | |
|---|---|---|---|---|---|---|---|---|
| Calculated | C | 55.42 | H | 5.74 | N | 7.60 | S | 8.70 |
| Found | | 55.22 | | 5.66 | | 7.53 | | 8.51 |

EXAMPLE 29

Ethyl [2-(2-(4-chlorobenzenesulphonylamino)-ethyl)-1-methylpyrrol-5-yl]-acetate

Prepared analogously to Example 28 from 2-(2-(4-chlorobenzenesulphonylamino)-ethyl)-1-methylpyrrole and ethyl diazoacetate.

Yield: 58% of theory,
Melting point: resin
R_f-value: 0.3 (silica gel - polygram plates; solvent: ethylene chloride : ethanol = 100:1)

EXAMPLE 30

Ethyl [2-(2-toluenesulphonylamino)-ethyl)-1-methylpyrrol-5-yl]-acetate

Prepared analogously to Example 28 from 2-(2-toluenesulphonylamino)-ethyl-1-methylpyrrole and ethyl diazoacetate.

Yield: 45% of theory,
Melting point: resin
R_f-value: 0.2 (silica gel - polygram plates; solvent: ethylene chloride : ethanol = 100:1)

EXAMPLE 31

Ethyl [2-(2-benzylsulphonylamino)-ethyl)-1-methylpyrrol-5-yl]-acetate

Prepared analogously to Example 28 from 2-(2-benzylsulphonylamino)-ethyl-1-methylpyrrole and ethyl diazoacetate.

Yield: 38% of theory,
Melting point: resin
R_f-value: 0.2 (silica gel - polygram plates; solvent: ethylene chloride : ethanol = 100:1)

EXAMPLE 32

[2-(2-(4-Fluorobenzenesulphonylamino)-ethyl)-1-methylpyrrol-5-yl]-acetic acid 0.5 g (1.3 mmol) of ethyl [2-(2-(4-fluorobenzenesulphonylamino)-ethyl)-1-methylpyrrol-5-yl]acetate are stirred into 4.5 ml of 1N sodium hydroxide solution overnight at ambient temperature. The mixture is then extracted with ethylene chloride and the aqueous phase is acidified with 1N hydrochloric acid. The precipitate obtained is suction filtered and dried.

Yield: 190 mg (43% of theory),
Melting point: 117°–121° C.

| C₁₅H₁₇FN₂O₄S (340.4) | | | | | | | |
|---|---|---|---|---|---|---|---|
| Calculated | C | 52.93 | H | 5.03 | N | 8.23 | |
| Found | | 52.93 | | 5.00 | | 7.96 | |

EXAMPLE 33

[2-(2-(4-Chlorobenzenesulphonylamino)-ethyl)-1-methylpyrrol-5-yl]-acetic acid

Prepared analogously to Example 32 from ethyl 4-[2-(2-(4-chlorobenzenesulphonylamino)-ethyl)-1-methyl-pyrrol-5-yl]acetate.

Yield: 35% of theory,
Melting point: 120°–125° C. (decomp.)

| C₁₅H₁₇ClN₂O₄S (356.8) | | | | | | | | |
|---|---|---|---|---|---|---|---|---|
| Calculated | C | 50.49 | H | 9.94 | N | 7.85 | S | 8.99 |
| Found | | 50.55 | | 10.01 | | 7.98 | | 9.23 |

EXAMPLE 34

[2-(2-(Toluenesulphonylamino)-ethyl)-1-methylpyrrol-5yl]-acetic acid

Prepared analogously to Example 32 from ethyl [2-(2-(toluenesulphonylamino)-ethyl)-1-methylpyrrol-5-yl]-acetate.

Yield: 28% of theory,
Melting Point: 118°–123° C. (decomp.)

| C₁₆H₂₀N₂O₄S (336.4) | | | | | | | | |
|---|---|---|---|---|---|---|---|---|
| Calculated | C | 57.12 | H | 5.99 | N | 8.33 | S | 9.53 |
| Found | | 57.30 | | 6.14 | | 8.45 | | 9.80 |

EXAMPLE 35

[2-(2-(Benzylsulphonylamino)-ethyl)-1-methylpyrrol-5-yl]-acetic acid

Prepared analogously to Example 32 from ethyl [2-(2-(benzylsulphonylamino)-ethyl)-1-methylpyrrol-5-yl]-acetate.

Yield: 31% of theory,
Melting point: 95°–100° C. (decomp.)

| C₁₆H₂₀N₂O₄S (336.4) | | | | | | | | |
|---|---|---|---|---|---|---|---|---|
| Calculated | C | 57.12 | H | 5.99 | N | 8.33 | S | 9.53 |
| Found | | 57.01 | | 6.14 | | 8.45 | | 9.33 |

EXAMPLE I

Tablets containing 100 mg of 4-[2-(2-(p-fluorobenzene sulphonylamino)-ethyl)-1-methyl-pyrro]-5-yl]-4-oxybutyric acid

| Composition | |
|---|---|
| 1 tablet contains | |
| Active substance | 100.0 mg |
| Lactose | 80.0 mg |
| Corn starch | 34.0 mg |
| Polyvinylpyrrolidone | 4.0 mg |
| Magnesium stearate | 2.0 mg |
| | 220.0 mg |

Method of preparation

The active substance, lactose and starch are mixed together and uniformly moistened with an aqueous solution of the polyvinylpyrrolidone. After the moist mass has been screened (2.0 mm mesh size) and dried in a rack drying cupboard at 50° C., it is screened again (1.5 mm mesh size) and the lubricant is added. The mixture ready for compressing is made into tablets.

Weight of tablet: 220 mg
Diameter: 9 mm, biplanar faceted on both sides and slotted on one side.

EXAMPLE II

Hard gelatine capsules containing 150 mg of 4-[2-(2-(p-fluorobenzenesulphonylamino)-ethyl)-1-methyl-pyrrol-5-yl]-4-oxybutyric acid

| 1 capsule contains | | |
|---|---|---|
| Active substance | | 150.0 mg |
| Dried corn starch | approx. | 180.0 mg |
| Powdered lactose | approx | 87.0 mg |
| Magnesium stearate | | 3.0 mg |
| | approx. | 320.0 mg |

Preparation

The active substance is mixed with the excipients, passed through a screen with a mesh size of 0.75 mm and homogeneously mixed in a suitable apparatus. The finished mixture is transferred into size 1 hard gelatine capsules.

Capsule filling: about 320 mg
Capsule casing: size 1 hard gelatine capsule

EXAMPLE III

Suppositories containing 150 mg of 4-[2-(2-(p-fluorobenzenesulphonylamino)-ethyl)-1-methylpyrrol-5-yl]-4-oxybutyric acid

| 1 suppository contains | |
|---|---|
| Active substance | 150.0 mg |
| Polyethylene glycol (M.W. 1500) | 550.0 mg |
| Polyethylene glycol (M.W. 6000) | 460.0 mg |
| Polyethylenesorbitan monostearate | 840.0 mg |
| | 2000.0 mg |

Preparation

After the suppository masses have been melted the active substance is homogeneously distributed therein and the melt is poured into chilled moulds.

EXAMPLE IV

Suspensions containing 50 mg of 4-[2-(2-(p-fluorobenzenesulphonylamino)-ethyl)-1-methylpyrrol-5-yl]-4-oxy-butyric acid

| 100 ml of suspension contains | |
|---|---|
| Active substance | 1.0 g |
| Na-salt of carboxymethyl cellulose | 0.2 g |
| Methyl p-hydroxybenzoate | 0.05 g |
| Propyl p-hydroxybenzoate | 0.01 g |
| Glycerol | 5.0 g |
| 70% Sorbitol solution | 50.0 g |
| Flavouring | 0.3 g |
| Distilled water | ad. 100 ml |

Preparation

Distilled water is heated to 70° C. The methyl- and propyl p-hydroxybenzoates and the glycerol and sodium salt of carboxymethyl cellulose are dissolved therein with stirring. The solution is cooled to ambient temperature and, whilst stirring, the active substance is added and homogeneously dispersed. After the sugar, sorbitol solution and flavouring have been added and dissolved the suspension is evacuated with stirring to eliminate air.

5 ml of suspension contains 50 mg of active substance.

Example V

Tablets containing 150 mg of 4-[2-(2-(p-fluorobenzenesulphonylamino)-ethyl)-1-methylpyrrol-5-yl]-4-oxybutyric acid

| Composition | |
|---|---|
| 1 Tablet contains | |
| Active substance | 150.0 mg |
| Powdered lactose | 89.0 mg |
| Corn starch | 40.0 mg |
| Colloidal silica | 10.0 mg |
| Polyvinylpyrrolidone | 10.0 mg |
| Magnesium stearate | 1.0 mg |
| | 300.0 mg |

Preparation

The active substance, mixed with lactose, corn starch and silica, is moistened with a 20% aqueous polyvinylpyrrolidone solution and passed through a screen with a mesh size of 1.5 mm. The granulate, dried at 45° C., is passed through the same screen again and mixed with the specified quantity of magnesium stearate. Tablets are compressed from the mixture.

Weight of tablet: 300 mg
Diameter: 10 mm, flat

EXAMPLE VI

Film-coated tablets containing 75 mg of 4-[2-(2-(p-fluorobenzenesulphonylamino)-ethyl)-1-methylpyrrol5-yl]-4-oxybutyric acid

| 1 Tablet core contains | |
|---|---|
| Active substance | 75.0 mg |
| Calcium phosphate | 93.0 mg |
| Corn starch | 35.5 mg |
| Polyvinylpyrrolidone | 10.0 mg |
| Hydroxypropylmethylcellulose | 15.0 mg |
| Magnesium stearate | 1.5 mg |
| | 230.0 mg |

Preparation

The active substance is mixed with calcium phosphate, corn starch, polyvinylpyrrolidone, hydroxypropylmethylcellulose and half the specified quantity of magnesium stearate. Blanks with a diameter of about 13 mm are produced in a tablet-making machine, these blanks are passed through a screen with a mesh size of 1.5 mm in a suitable machine and then mixed with the remainder of the magnesium stearate. This granulate is compressed in a tablet-making machine to form tablets of the desired shape.

Weight of core: 230 mg
Diameter: 9 mm, convex

The tablet cores just produced are coated with a film consisting essentially of hydroxypropylmethyl cellulose.

The finished film-coated tablets are polished with bees wax.

Weight of film-coated tablet: 245 mg

Obviously, all the other compounds of general formula I may be used as active substances in the galenic preparations described hereinbefore.

What is claimed is:

1. Sulphonamidoethyl compounds of formula

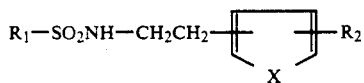

(I)

wherein $R_1$ is phenyl optionally mono-, di- or trisubstituted by halo, methyl or methoxy, where the substituents may be the same or different, or benzyl, nitrophenyl, acetamidophenyl or thienyl, $R_2$ is hydroxycarbonyl or alkoxycarbonyl with a total of 2 to 4 carbon atoms bonded via straight chained or branched $C_1$–$C_5$ alkylene or via $C_2$–$C_5$ alkenylene, whilst any methylene group in the above-mentioned alkylene or alkenylene groups, which must be liked to the heterocyclic group, may be replaced by hydroxymethylene or carbonyl, and X is oxygen, the enantiomers and salts thereof with inorganic or organic bases, if $R_2$ comprises hydroxycarbonyl.

2. The sulphonamidoethyl compounds as recited in claim 1, wherein $R_1$ is phenyl optionally monosubstituted by methyl, methoxy or nitro, or phenyl mono-, di or trisubstituted by fluoro, chloro or bromo atoms, and $R_2$ is hydroxycarbonylmethyl, ethoxycarbonylmethyl, 2-ethoxycarbonyl-ethyl, 3-hydroxycarbonyl-n-propan-(1)-yl, 3-methoxycarbonyl-n-propan-(1)-yl, 3-hydroxycarbonyl-n-propan-1-on-(1)-yl, or 3-methoxy-carbonyl-n-propan-1-on-(1)-yl and X is oxygen, the enantiomers and salts thereof with inorganic or organic bases, if $R_2$ comprises hydroxycarbonyl.

3. The sulphonamidoethyl compounds as recited in claim 1 wherein $R_1$ is phenyl optionally monosubstituted by fluoro or chloro or by methyl or methoxy, and $R_2$ is hydroxycarbonylmethyl or 3-hydroxycarbonyl-n-propan-1-on-(1)-yl and X is oxygen, the enantiomers and salts thereof with inorganic or organic bases, if $R_2$ comprises hydroxycarbonyl.

4. A pharmaceutical composition of matter comprising a compound as recited in claim 1 together with one or more pharmaceutically acceptable carriers or diluents.

5. A method for treatment of thromboembolic disorders in a warm-blooded animal which comprises administering to said animal a therapeutically acceptable amount of a compound as recited in claim 1.

6. A method for prophylaxis of thromboembolic disorders in a warm-blooded animal which comprises administering to said animal a therapeutically acceptable amount of a compound as recited in claim 1.

* * * * *